United States Patent [19]

Katoh et al.

[11] Patent Number: 4,927,827
[45] Date of Patent: May 22, 1990

[54] PYRIDINYLPYRIMIDINE DERIVATIVES, METHOD FOR PRODUCTION THEREOF AND A FUNGICIDE CONTAINING THEM AS THE ACTIVE INGREDIENT

[75] Inventors: Tsuguhiro Katoh, Osaka; Kiyoto Maeda; Masao Shiroshita, both of Hyogo; Norihisa Yamashita, Osaka; Yuzuru Sanemitsu; Satoru Inoue, both of Hyogo; Masayo Sugano, Osaka; Hirotaka Tanako, Hyogo, all of Japan

[73] Assignee: Sumitomo Chemical Company, Limited, Osaka, Japan

[21] Appl. No.: 195,977

[22] Filed: May 19, 1988

[30] Foreign Application Priority Data

May 19, 1987 [JP] Japan ............................... 62-123188

[51] Int. Cl.$^5$ ................. C07D 239/34; C07D 239/26; A01N 43/54
[52] U.S. Cl. .................................. 514/256; 544/333; 544/319; 514/269
[58] Field of Search .................. 514/256, 269; 544/333, 544/319

[56] References Cited

U.S. PATENT DOCUMENTS 4,752,608  6/1988  Katoh et al. ............... 544/333
4,783,466 11/1988  Katoh et al. ............... 544/333
4,822,798  4/1989  Stoltefuss et al. .......... 544/333

FOREIGN PATENT DOCUMENTS 49-11709  3/1974  Japan ........................ 544/333

OTHER PUBLICATIONS

W. Fife, "Ayanation in the Pyridine Series: . . . Reactions", Heterocycles, vol. 22, No. 10 (1984), pp. 2375-2394.
W. Fife, "Regioselective Cyanation . . . Reaction", J. Org. Chem., vol. 48 (1983), pp. 1375-1377.
H. Vorbruggen et al., "Trimethylsilanol as Leaving Group; . . . N–Heterocycles", Synthesis (4/83), pp. 316-318.
J. Lafferty et al., "The Preparation and Properties . . . Iron(II)", J. Org. Chem., vol. 32 (1967), pp. 1591-1596.
D. Brown et al., "Unfused Heterobicycles as . . . Chains", Aust. J. Chem., vol. 35 (1982), pp. 1203-1207.
D. Brown et al., "Unfused Heterobicycles as . . . Thaizolylpyridines", Aust. J. Chem., vol. 33 (1980), pp. 2291-2299.
T. Sakamoto et al., "Site-Selectivity in the Cyanation . . . Trimethylsilanecarbonitrile", Chem. Pharm. Bull., vol. 33, No. 2 (1985), pp. 565-571.

Primary Examiner—John M. Ford
Attorney, Agent, or Firm—Sughrue, Mion, Zinn, Macpeak & Seas

[57] ABSTRACT

A novel pyridinylpyrimidine derivative of the formula below, a method for preparation thereof and a fungicide containing it,

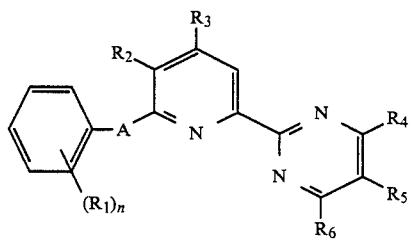

which is effective as a fungicide.

6 Claims, No Drawings

PYRIDINYLPYRIMIDINE DERIVATIVES, METHOD FOR PRODUCTION THEREOF AND A FUNGICIDE CONTAINING THEM AS THE ACTIVE INGREDIENT

This invention relates to a novel pyridinylpyrimidine derivative, a method for preparation thereof and a fungicide containing it as an active ingredient.

The pyridinylpyrimidine derivatives such as 4-methyl-2-(2-pyridinyl)pyrimidine (J. Org. Chem. 32, 1591, (1967)) and N,N-dimethyl-2-(6-methyl-2-pyridylpyrimidine-4-yl-thio)-ethyl amine (Aust. J. Chem., 35 1203 (1982)) are known.

However, it is not known that the pyridinylpyrimidine derivatives have fungicidal effect at all.

An object of the present invention is to provide a compound having preventive and curative controlling effects against many plant diseases.

The present inventors have found that pyridinylpyrimidine derivatives having the formula (I) mentioned below or a salt thereof (hereinafter referred simply to as the present compound) have excellent fungicidal activity:

$$\text{(I)}$$

wherein $R_1$ may be the same or different and is an alkyl group, an alkoxy group, an alkyl thio group, a cyano group, a carboalkoxy group, a halo alkyl group, a phenyl group, or halogen atom; n is 0, 1, 2, 3, 4, or 5; A is oxygen atom or sulfur atom; $R_2$, $R_3$, $R_4$ and $R_5$, which may be the same or different, each represent hydrogen atom or an alkyl group; $R_6$ is hydrogen atom, an alkyl group, an alkoxy group, an alkenyloxy group or an alkynyloxy group.

Preferably, $R_1$ may be the same or different and is a lower such as $C_1$–$C_4$ alkyl group, a lower such as $C_1$–$C_3$ alkoxy group, a lower such as $C_1$–$C_3$ alkyl thio group, a cyano group, a carboalkoxy group whose alkoxy is a lower such as $C_1$–$C_3$ alkoxy group, a lower such as $C_1$–$C_3$ halo alkyl group, a pheny group, or halogen atom; n is 0, 1, 2, 3, 4 or 5; A is oxygen atom or sulfur atom; $R_2$ and $R_3$ which may be the same or different, each represent hydrogen atom, a methyl or ethyl group; $R_4$ and $R_5$ which may be the same or different, each represent hydrogen atom or a lower such as $C_1$–$C_3$ alkyl group; $R_6$ is hydrogen atom, a lower such as $C_1$–$C_4$ alkyl group, a lower such as $C_1$–$C_4$ alkoxy group, a lower such as $C_3$–$C_4$ alkenyloxy group or a lower such as $C_3$–$C_4$ alkynyloxy group.

More preferably, $R_1$ may be the same or different and is a lower such as $C_1$–$C_3$ alkyl group, a methoxy group, an ethoxy group, a methylthio group, a lower such as $C_1$–$C_2$ haloalkyl group, or halogen atom; n is 0, 1, 2 or 3; A is oxygen atom; $R_2$ and $R_3$ which may be the same or different, each represent hydrogen atom or a methyl group; $R_4$ is a lower such as $C_1$–$C_3$ alkyl group; $R_5$ is hydrogen atom or a methyl group; $R_6$ is hydrogen atom, a methyl group, or a methoxy group.

Most preferably, $R_1$ may be the same or different and is a methyl group, a methoxy group, an ethoxy group, a trifluoromethyl group, fluorine, chlorine, or bromine atom; n is 0, 1 or 2; A is oxygen atom; $R_2$ and $R_3$ which may be the same or different, each represent hydrogen atom or a methyl group; $R_4$ is a methyl group; $R_5$ and $R_6$ are hydrogen atoms, respectively.

Plant disease that are controlled by the present compound include the followings;

Rice: *Pyricularia oryzae*, *Cochliobolus miyabeanus* and *Rhizoctonia solani*;

Barley and wheat: *Erysiphe graminis* f. sp. hordei, *E. graminis* f. sp. tritici, *Pyrenophora teres*, *Pyrenophora graminea*, *Puccinia striiformis*, *P. graminis*, *P. recondita*, *P. hordei*, *Pseudocercosporella herpotrichoides*, *Rhynchosporium secalis*, *Septoria tritici*, *Leptosphaeria nodorum* and *Fusarium nivale*;

Citrus: *Diaporthe citri* and *Elsinoe fawcetti*;

Apple: *Podosphaera leucotricha*, *Alternaria mali* and *Venturia inaequalis*;

Pear: *Venturia nashicola* and *Alternaria kikuchiana*;

Peach: *Sclerotinia cinerea*;

Grape: *Elsinoe ampelina*, *Glomerella cingulata* and *Uncinula necator*;

Melon crops: *Colletotrichum lagenarium* and *Sphaerotheca fuliginea*;

Tomato: *Alternaria solani* and *Phytophthora infestans*;

Eggplant: *Phomopsis vexans*;

Rape: *Alternaria japonica* and *Cercosporella brassicae*;

Welsh onion: *Puccinia allii*;

Soybean: *Cercospora kikuchii* and *Elsinoe glycines*;

Kidney bean: *Colletotrichum lindemuthianum*;

Peanut: *Mycosphaerella personatum* and *Cercospora arachidicola*;

Pea: *Erysiphe pisi*;

Potato: *Alternaria solani*;

Sugar beet: *Cercospora beticola*;

Rose: *Diplocarpon rosae* and *Sphaerotheca pannosa*;

Crop plants: *Botrytis cinerea* and *Sclerotinia sclerotiorum*.

Diseases more controllable among the above are

Rice: *Pyricularia oryzae*,

Barley and wheat: *Septoria tritici*, *Pseudocercosporella herpotrichoides*, *Pyrenophora teres*, and most controllable is

*Pyricularia oryzae* against rice.

The pyridinylpyrimidine derivative (I) is typically prepared by the methods as shown below:

Procedure (a):

A pyridinylpyrimidine derivative of the formula:

$$\text{(II)}$$

wherein $R_1$, $R_2$, $R_3$, $R_4$, $R_5$, A and n arethe same as defined above and $R_6'$ is hydrogen atom, is obtained by allowing a picoline amidine derivative of the formula:

(III)

[Chemical structure III: pyridine bearing R2, R3 substituents, A-linked phenyl with (R1)n, and a C(=NH)NH2 amidine group]

wherein R1, R2, R3, A and n are the same as defined above, or a salt thereof to react, in the presence of a base, with β-oxoacetal derivative of the formula:

$$R_4-\underset{\underset{O}{\|}}{C}CHCH(OR_7)_2 \quad \overset{R_5}{|} \qquad (IV)$$

wherein R4 and R5 are the same as defined above and R7 is a lower such as C1–C4 alkyl group.

Examples of the salt of picoline amidine derivative are hydrochloride, hydrobromide, acetate and formate. Examples of such base are alkali metal alkoxide such as sodium methoxide and sodium ethoxide and organic base such as triethylamine and N,N-diethylaniline. Sodium methoxide or sodium ethoxide is preferable.

The reaction is usually carried out in the presence of an inert solvent such as lower alcohol (e.g. methanol and ethanol), cyclic ether (e.g. dioxane and tetrahydrofuran), pyridine and N,N-dimethylformamide. The reaction may be carried out at about 50°–150° C. for about 1–6 hours.

The β-oxoacetal derivative (IV) and the base may be used in amounts of about 1 to 1.5 equivalent and about catalytic amount to 2.5 equivalent, respectively, to 1 equivalent of the picoline amidine derivative (III) or its salt.

After the reaction is over, the reaction mixture is treated in a usual manner, such as concentration under reduced pressure, if necessary, chromatography to obtain the pyridinylpyrimidine derivative (II).

Procedure (b):

A pyridinylpyrimidine derivative of the formula:

[Chemical structure V: pyridine-pyrimidine compound with R6″ substituent]

wherein R1, R2, R3, R4, R5, A and n are the same as defined above and R6″ is an alkoxy group, an alkenyloxy group or an alkynyloxy group, is obtained by allowing the halopyrimidine derivative of the formula:

[Chemical structure VI: halopyrimidine compound with X halogen]

wherein R1, R2, R3, R4, R5, A and n are the same as defined above and X is halogen, to react with an alkali metal compound of the formula:

$$R_6''Y \qquad (VII)$$

wherein R6″ is defined above and Y is alkali metal.

Examples of the alkali metal are sodium, potassium, etc.

The reaction may be carried out at about 10°–120° C. for about 1 to 48 hours.

The alkali metal compound (VII) is usually used in an amount of about 1 to 1.5 equivalent to 1 equivalent of the halopyrimidine derivative (VI).

The reaction is usually carried out in the presence of a solvent such as an alcohol (corresponding to R6″ moiety; e.g. methanol, ethanol, allyl alcohol or propargyl alcohol), an ether (e.g. diethyl ether, dioxane or tetrahydrofuran) or a mixture thereof.

After the reaction is over, the reaction mixture is concentrated in vacuo. The residue obtained is subjected to a usual post-treatment such as extraction with organic solvent, concentration, and, if necessary, chromatography to obtain the objective compound (V).

Procedure (c):

A pyridinylpyrimidine derivative of the formula:

[Chemical structure VIII: pyridinylpyrimidine with R6‴ substituent]

wherein R1, R2, R3, R4, R5, A and n are the same as defined above and R6‴ is an alkyl group, is obtained by allowing the halopyrimidine derivative (VI) to react, in the presence of a base, with a diester derivative of the formula:

$$R_8CH(COOR_9)_2 \qquad (IX)$$

wherein R8 is hydrogen atom, or an alkyl group and R9 is a lower alkyl group, followed by hydrolysis and decarbonation.

Examples of the base are alkali metal hydride (e.g. sodium hydride), alkyl lithium (e.g. n-butyl lithium), lithium dialkylamide (e.g. lithium diisopropylamide (LDA)) and alkali metal hydroxide (e.g. sodium hydroxide).

The reaction may be carried out at about 0°–150° C. for about 0.5–24 hours.

The diester derivative (IX) and the base are usually used in amounts of about 1 to 2 equivalent, respectively, to 1 equivalent of the halopyrimidine derivative (VI).

The reaction is usually carried out in the presence of an inert solvent, e.g. nitriles such as acetonitrile; ethers such as diethylether or tetrahydrofuran; halohydrocarbons such as chloroform; aromatic hydrocarbons such as benzene or toluene; haloaromatic hydrocarbons such as chlorobenzene; ketones such as acetone or methylisobutyl ketone; esters such as ethylacetate; sulfur compounds such as dimethylsulfoxide and sulfolane or mixture thereof.

After the reaction is over, the reaction mixture is subjected to a hydrolysis reaction and a decarbonation reaction to obtain the pyridinylpyrimidine derivative (VIII). The hydrolysis and the decarbonation are typically carried out in the manner as shown below.

To the reaction mixture is added about 2.1 to 5 equivalent of the base to 1 equivalent of the halopyrimidine derivative (VI) in the form of an aqueous solution or an aqueous lower alcohol (e.g. methanol or ethanol) solution at about 10°–100° C. for a period from about 10 minutes to 24 hours. Examples of the base are alkali metal hydroxide (e.g. sodium hydroxide) and alkali metal carbonate (e.g. sodium carbonate).

Into the reaction mixture obtained above is added about 2.5 to 6 equivalent of acid to 1 equivalent of the used halopyrimidine derivative (VI) for the decarbonation reaction. The decarbonation reaction may be carried out at about 20°–150° C. for a period from about 10 minutes to 24 hours.

Examples of the acid are inorganic acid such as sulfuric acid or hydrochloric acid and organic acid such as acetic acid.

After the reaction is over, the reaction mixture is firstly neutralized with alkali metal hydroxide such as sodium hydroxide, alkaline earth metal hydroxide such as calcium hydroxide, alkali metal carbonate such as sodium carbonate or sodium bicarbonate, or organic base such as triethylamine.

Then, the reaction mixture is treated in a usual manner such as concentration and extraction, if necessary, recrystallization and column chromatography to obtain the pyridinylpyrimidine derivative (VIII).

Procedure (d):

A pyridinylpyrimidine derivative of the formula:

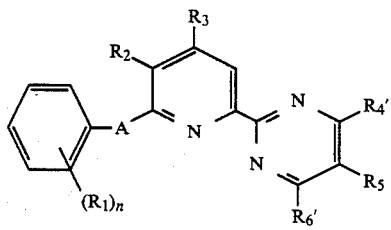

(X)

wherein $R_1$, $R_2$, $R_3$, $R_5$, A and n are the same as defined above and $R_4'$ and $R_6'$ are each hydrogen atom, is obtained by allowing a salt of picoline amidine derivative (III) to react with acetal derivative of the formula:

(XI)

wherein $R_5$ is the same as defined above and $R_{10}$ is a lower alkyl group.

The reaction may be carried out at about 50°–150° C. for about 1–6 hours in the absence of a solvent.

The acetal derivative (XI) may be used in an amount of about 1 to 3 equivalent to 1 equivalent of the picoline amidine derivative (III) or a salt thereof.

After the reaction is over, the reaction mixture is treated in a usual manner, such as concentration under reduced pressure, if necessary, chromatography to obtain the pyridinylpyrimidine derivative (X).

Procedure (e):

A pyridinylpyrimidine derivative of the formula (II) is obtained by allowing a pyridinylpyrimidine derivative of the formula:

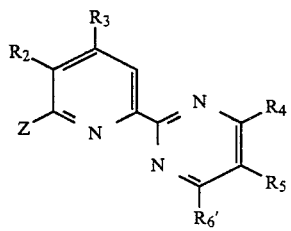

(XII)

wherein $R_2$, $R_3$, $R_4$ and $R_5$ are the same as defined above and Z is halogen atom and $R_6'$ is hydrogen atom to react, in the presence of a base, with benzene derivative of the formula:

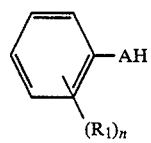

(XIII)

wherein $R_1$, A and n are the same as defined above.

Examples of the base are alkali metal (e.g. metallic sodium), alkali metal hydroxide (e.g. sodium hydroxide), sodium carbonate, potassium carbonate, alkali metal hydride (e.g. sodium hydride).

The reaction may be carried out at about 0° to 250° C. (preferably about 50° to 200° C.) for about 30 minutes to 100 hours.

The benzene derivative (XIII) and the base are usually used in an amount of about 1 to 5 equivalent to 1 equivalent of the pyridinylpyrimidine derivative (XII).

The reaction is usually carried out in the presence of an inert solvent such as N,N-dimethylformamide, dimethyl sulfoxide or sulforane.

In the reaction system, a catalytic substance may be present in order to accomplish the reaction smoothly. The catalytic substance, of which examples are copper and its compounds (e.g. metal copper, copper oxide, cuprous chloride and cupric chloride), may be used in an amount of about 0.01 to 5 equivalent to 1 equivalent of the pyridinylpyrimidine derivative (XII).

After the reaction is over, the reaction mixture is concentrated in vacuo. The residue obtained is subjected to a usual post-treatment such as extraction with organic solvent, concentration, and, if necessary, chromatography to obtain the objective compound (II).

The present compound having the formula (I) is easily converted to salts thereof by allowing the compound to react with plant-physiologically acceptable acids such as hydrochloric acid, hydrobromic acid, sulfuric acid or nitric acid.

The salt is typically obtained by the procedure shown below. The compound of the formula (I) is dissolved in a solvent and then one equivalent of the acid in the form of gas or aqueous solution is added thereto under ice cooling or at room temperature. After being left to stand for about 10 minutes to one hour, the solution is subjected to a post-treatment such as concentration under reduced pressure, and if necessary recrystallization. Examples of the solvent are lower alcohol such as methanol or ethanol; aromatic hydrocarbon such as toluene or benzene; ether such as ethyl ether, tetrahydrofuran or dioxane; halogenated hydrocarbon such as chloroform; ketone such as acetone; ester such as ethyl acetate; hydrocarbon such as hexane; water or a mixture thereof.

Picoline amidine derivative of the formula (III) and halopyrimidine derivative of the formula (VI) are typically prepared by the following reaction scheme:

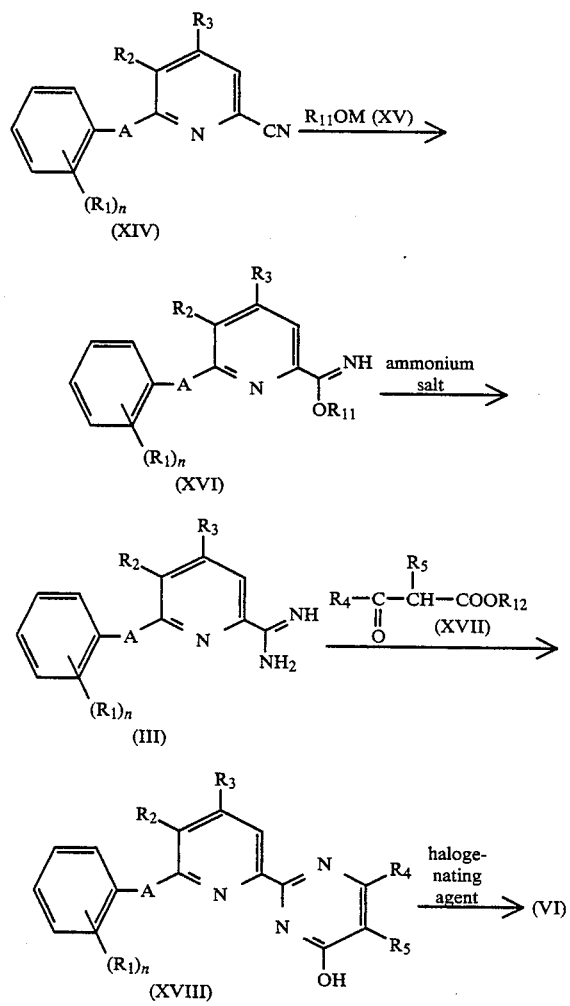

wherein $R_1$, $R_2$, $R_3$, $R_4$, $R_5$, A and n are the same as defined above, $R_{11}$ and $R_{12}$ each represent a lower alkyl group and M is alkali metal.

An imidate derivative of the formula (XVI) is prepared by allowing a cyanopyridine derivative of the formula (XIV), which is prepared by a method described in J. Org. Chem., 48, 1375–1377 (1983), to react with an alkoxide of the formula (XV). The picoline amidine of the formula (III) is prepared by allowing the imidate derivative of the formula (XVI) to react with an ammonium salt, followed by decomposition of a salt of the amidine derivative of the formula (III) obtained. A hydroxypyrimidine derivative of the formula (XVIII) is obtained by allowing the picoline amidine derivative of the formula (III) or a salt thereof to react, in the presence of a base, with β-oxocarboxylate of the formula (XVII). The halopyrimidine derivative of the formula (VI) is obtained by allowing the hydroxypyrimidine derivative of the formula (XVIII) to react with a halogenating agent.

Details of the above production are as follows.

A reaction between the compound of the formula (XIV) and the compound of the formula (XV):

Examples of alkali metal atom in the alkoxide (XV) are sodium atom, potassium atom, etc. The reaction is usually carried out in the presence of a solvent at about 10° to 50° C. for about 1 to 48 hours. The alkoxide (XV) may be used in an amount of about 0.1 to 1 equivalent to 1 equivalent of the cyanopyridine derivative (XIV). As the solvent, there may be used, for example, a lower alcohol corresponding to $R_{11}$ of the alkoxide (XV), (e.g. methyl alcohol, ethyl alcohol, n-propyl alcohol, isopropyl alcohol or n-butyl alcohol), preferably methyl alcohol or ethyl alcohol.

After the reaction is over, neutralization of the solution is effected with acid, concentrated under reduced pressure and dissolved in an organic solvent. After insoluble alkali metal salt is filtered out, the filtrate is concentrated in vacuo, and, if necessary, distilled to obtain the imidate derivative (XVI).

A reaction between the compound (XVI) and ammonium salt:

In this step, ammonium salt used is that of, for example, hydrochloric acid, hydrobromic acid, acetic acid or formic acid.

The reaction is usually carried out in the presence of a solvent at 30°–100° C. for 0.5–5 hours. The ammonium salt may be used in amounts of 1 to 1.1 equivalent to 1 equivalent of the imidate derivative (XVI). As the solvent, there may be used, for instance, a lower alcohol, preferably a solution of ethanol or water.

After the reaction is over, the reaction mixture may be concentrated in vacuo and, if necessary recrystallized to obtain such salt as hydrochloride, hydrobromide, acetate or formate of picoline amidine derivative of the formula (III). The salt is decomposed by a usual manner such as neutralization with an inorganic base, for example sodium hydroxide, potassium hydroxide, sodium methoxide or sodium ethoxide, to obtain picoline amidine derivative of the formula (III).

Alternatively, the salt may be subjected, as it is, to the next step where decomposition thereof is effected.

Reaction between picoline amidine derivative having the formula (III) or a salt thereof and the β-oxocarboxylate having the formula (XVII):

The reaction is usually carried out in the presence of a solvent at about 50°–150° C. for about 1–24 hours. The β-oxocarboxylate (XVII) may be used in an amount of 1 to 1.5 equivalent to 1 equivalent of the picoline amidine derivative (III) or a salt thereof. The base may be used from a catalytic amount to 1.5 equivalent to 1 equivalent of the picoline amidine derivative (III) or a salt thereof.

As the solvent, there may be used, for instance, lower alcohol such as methanol or ethanol, cyclic ether such as dioxane, tetrahydrofuran, pyridine, N,N-dimethylformamide, water or a mixture thereof.

As the base, there may be used, for instance, inorganic base such as sodium hydroxide, potassium hydroxide, potassium carbonate, or organic one such as alkali metal alkoxide such as sodium methoxide, triethylamine or N,N-diethylaniline. After the reaction is over, in case of using the salt of picoline amidine derivative of the formula (III), the by-produced inorganic salt is filtered out, and the filtrate is concentrated in vacuo to obtain a residue. The residue may be treated by chromatography or recrystallization to obtain the hydroxypyrimidine derivative (XVIII).

Reaction between the hydroxypyrimidine derivative having the formula (XVIII) and the halogenating agent:

As the halogenating agent, there may be used, for instance, thionyl chloride, phosgene, phosphoryl chloride, phosphorus pentachloride, phosphoryl bromide or phosphorus tribromide.

The reaction is usually carried out in the presence of a solvent at about 50°-150° C. for about 1-10 hours. The halogenating agent may be used in an amount of about 1 to 10 equivalent to 1 equivalent of the hydroxypyrimidine derivative (XVIII). As the solvent, there may be used, for instance, aromatic hydrocarbons (e.g. benzene or toluene), halogenated hydrocarbons (e.g. chlorobenzene), etc.

After the reaction is over, a post-treatment of the reaction mixture may be carried out in a usual manner. For instance, the reaction mixture is concentrated under reduced pressure and neutralized with an inorganic base (e.g. sodium hydroxide). Then, the above mixture is extracted with an organic solvent and the extract is concentrated in vacuo to obtain the halopyrimidine derivative (VI). Any further procedure such as chromatography or recrystallization may be applied, if necessary, to the resultant product.

Pyridinylpyrimidine derivative (XII) is typically prepared by the following scheme:

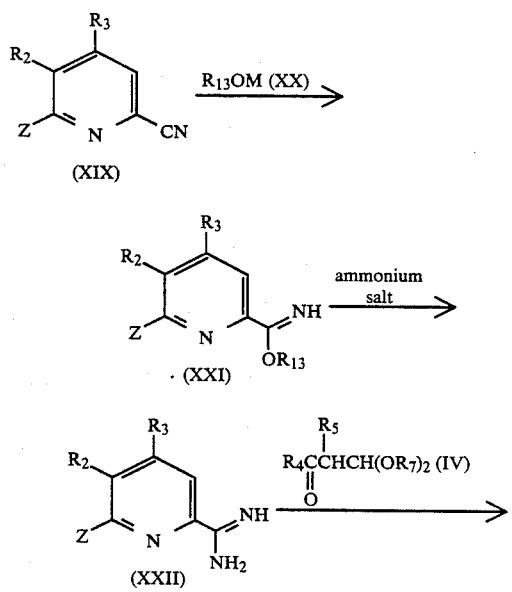

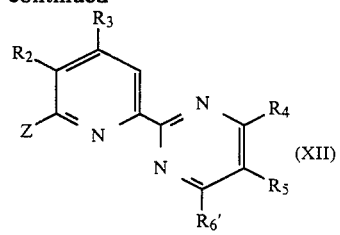

wherein $R_2$, $R_3$, $R_4$, $R_5$, $R_6'$, $R_7$ and Z are the same as defined above, and $R_{13}$ is a lower alkyl group.

Cyanopyridine derivative (XIX) is prepared by a method described in Chem. Pharm. Bull., 33(2), 565–571 (1985).

Imidate derivative (XXI), picoline amidine derivative (XXII), and pyridinylpyrimidine derivative (XII) are prepared by the same method each as described for (XVI), (III) and (II).

Details of the above production are as follows.

A reaction between the compound of the formula (XIX) and the compound of the formula (XX):

Examples of alkali metal atom in the alkoxide (XX) are sodium atom, potassium atom, etc. The reaction is usually carried out in the presence of a solvent at 10° to 30° C. for 5 minutes to 2 hours. The alkoxide (XX) may be used in an amount of 0.1 to 1 equivalent to 1 equivalent of the cyanopyridine derivative (XIX). As the solvent, there may be used, for example, a lower alcohol corresponding to $R_{13}$ of the alkoxide (XX), (e.g. methyl alcohol, ethyl alcohol, n-propyl alcohol, isopropyl alcohol or n-butyl alcohol), preferably methyl alcohol or ethyl alcohol.

After the reaction is over, neutralization of the solution is effected with acid, concentrated under reduced pressure and dissolved in an organic solvent. After insoluble alkali metal salt is filtered out, the filtrate is concentrated in vacuo, and, if necessary, distilled to obtain the imidate derivative (XXI).

A reaction between the compound (XXI) and ammonium salt:

In this step, ammonium salt used is that of, for example, hydrochloric acid, hydrobromic acid, acetic acid or formic acid.

The reaction is usually carried out in the presence of a solvent at 30°-100° C. for 0.5-5 hours. The ammonium salt may be used in amounts of 1 to 1.1 equivalent to 1 equivalent of the imidate derivative (XXI). As the solvent, there may be used, for instance, a lower alcohol, preferably a solution of ethanol or water.

After the reaction is over, the reaction mixture may be concentrated in vacuo and, if necessary recrystallized to obtain such salt as hydrochloride, hydrobromide, acetate or formate of picoline amidine derivative of the formula (XXII). The salt is decomposed by a usual manner such as neutralization with an inorganic base, for example sodium hydroxide, potassium hydroxide, sodium methoxide or sodium ethoxide, to obtain picoline amidine derivative of the formula (XXII).

Alternatively, the salt may be subjected, as it is, to the next step where decomposition thereof is effected.

Reaction between picoline amidine derivative having the formula (XXII) or a salt thereof and the β-oxoacetal having the formula (IV):

The reaction is usually carried out in the presence of a solvent at 50°-150° C. for 1-3 hours. The β-oxoacetal (IV) may be used in an amount of 1 to 1.5 equivalent to 1 equivalent of the picoline amidine derivative (XXII) or a salt thereof. The base may be used from a catalytic amount to 1.5 equivalent to 1 equivalent of the picoline amidine derivative (XXII) or a salt thereof.

As the solvent, there may be used, for instance, lower alcohol such as methanol or ethanol, cyclic ether such as dioxane, tetrahydrofuran, pyridine, N,N-dimethylformamide or a mixture thereof.

Examples of such base are alkali metal alkoxide such as sodium methoxide and sodium ethoxide and organic base such as triethylamine and N,N-diethylaniline. Sodium methoxide or sodium ethoxide is preferable.

After the reaction is over, the reaction mixture is treated in a usual manner, such as concentration under reduced pressure, if necessary, chromatography to obtain the pyridinylpyrimidine derivative (XII).

The pyridinylpyrimidine derivatives of this invention may be used as an active ingredient of a plant disease protectant, and it is usually mixed with a solid carrier, a liquid carrier, a surface active agent, and other adjuvants and formulated into emulsion, wettable powder, suspension, granule, dust, or liquid.

These formulations may contain the pyridinylpyrimidine derivative in a concentration of about 0.1 to 99% by weight, preferably about 0.2 to 95% by weight.

Examples of solid carriers include kaolin clay, attapulgite clay, bentonite, Japanese acid clay, pyrophyllite, talc, diatomaceous earth, calcite, corncob powder, walnut shell powder, urea, ammonium sulfate, and synthetic hydrated silica, which are in the form of finely divided powder or granule. Examples of liquid carrier include aromatic hydrocarbons, e.g., xylene and methylnaphthalene; alcohols, e.g., isopropanol, ethylene glycol, and cellosolve; ketones, e.g., acetone, cyclohexanone, and isophorone; vegetable oils e.g., soybean oil and cottonseed oil; dimethylsufoxide, acetonitrile or water.

Examples of surface active agents for emulsification, dispersion, and wetting include anionic surface active agents such as alkyl sulfate salt, alkyl or aryl sulfonate, dialkylsulfosuccinate, polyoxyethylene alkylarylether phosphate salt, and naphthalene sulfonic acid-formalin condensate; and nonionic surface active agents such as polyoxyethylene alkyl ether, polyoxyethylene-polyoxypropylene block copolymer, sorbitanfatty acid ester or polyoxyethylene-sorbitan fatty acid ester. Examples of adjuvants include ligninsulfonate, alginate, polyvinyl alcohol, gum arabic, CMC (carboxymethylcellulose) or PAP (isopropyl acidphosphate).

These formulations are used as such or after dilution with water for foliage application or soil treatment or soil incorporation. They may also be used in combination with other plant disease protectants for their enhanced control effect. Further, they may be used in combination with an insecticide, acaricide, nematicide, herbicide, plant growth regulator, fertilizer, and soil conditioner.

In the case where the present compound is used as an active ingredient of a plant disease protectant, the dosage varies depending on the weather conditions, formulation, application time, application method, application place, object diseases, and object crops. The dosage is usually about 0.2 to 200 g, preferably about 1 to 100 g for an area of 1 are. In the case of emulsion, wettable powder, suspension, or liquid formulation which is diluted with water prior to application, the concentration should be about 0.005 to 0.5%, preferably about 0.01 to 0.2% by weight. Granules and dusts are used as such without dilution.

The present invention is explained in further detail referring to synthesis examples, formulation examples and efficiency tests.

Synthesis examples of the present compound

EXAMPLE 1

To a mixture of 6-o-tolyloxy-2-picoline amidine hydrochloride (3 g) and methanol (100 ml) were added 28% sodium methoxide solution in methanol (3.3 g) and 1,1-dimethoxybutanone (1.9 g). The mixture was heated under refluxing for an hour, and was left to stand at room temperature. The reaction solution was concentrated under reduced pressure, and the residue obtained was subjected to silica gel column chromatography (eluent; n-hexane: ethyl acetate=2:1 in volume) to obtain 4-methyl-2-(6-o-tolyloxy-2-pyridinyl)pyrimidine (2.4 g, yield 76%).

m.p. 121.0° C.

PMR (CDCl$_3$) δ ppm: 2.24 (s, 3H, —CH$_3$) 2.63 (s, 3H, —CH$_3$) 7.70 (t, 1H, pyridine-H$^4$, J=7.8 Hz) 8.15 (d, 1H, pyridine-H$^3$, J=7.8 Hz) 8.69 (d, 1H, pyrimidine-H$^6$, J=5.4 Hz).

EXAMPLE 2

To 4-chloro-2-(6-p-ethoxyphenyloxy-2-pyridinyl)-6-methylpyrimidine (3 g) was added sodium methoxide prepared from methanol (10 ml) and metallic sodium (0.22 g). After the mixture was left to stand at room temperature for 30 minutes, water (30 ml) and chloroform (100 ml) were added thereto, and then extracted. After the extract was dried over anhydrous magnesium sulfate, it was concentrated under reduced pressure to obtain 2-(6-p-ethoxyphenyloxy-2-pyridinyl)-4-methoxy-6-methylpyrimidine (2.7 g, yield 91%).

m.p. 135.8° C.

PMR (CDCl$_3$) δ ppm: 1.40 (t, 3H, —CH$_2$CH$_3$, J=6.6 Hz) 2.51 (s, 3H, —CH$_3$) 4.00 (q, 2H, —CH$_2$CH$_3$, J=6.6 Hz) 4.02 (s, 3H, —OCH$_3$) 6.51 (s, 1H, pyrimidine-H$^5$) 7.70 (t, 1H, pyridine-H$^4$, J=7.8 Hz) 8.12 (d, 1H, pyridine-H$^3$, J=7.8 Hz).

EXAMPLE 3

To tetrahydrofuran (30 ml) were added diethyl malonate (1.35 g) and 60% oilly sodium hydride (0.34 g), and then 4-chloro-2-(6-o-chlorophenoxy-2-pyridinyl)-6-n-propylpyrimidine (2 g). The mixture was heated under refluxing for 30 minutes. Sodium hydroxide (0.72 g) solution in water (10 ml) and methanol (10 ml) were added thereto, and the mixture was further heated under refluxing for 20 minutes. After the mixture was left to stand until it was cooled to room temperature, sulfuric acid (1.2 g) was added dropwise thereto. The mixture was heated under refluxing for 30 minutes and left to stand to room temperature. 1-N aqueous sodium carbonate solution was added until a mixture was neutralized, and concentrated under reduced pressure. The residue was subjected to silica-gel column chromatography (eluent; n-hexane: ethyl acetate=2:1 in volume) to give 2-(6-o-chlorophenoxy-2-pyridinyl)-4-methyl-6-n-propylpyrimidine (1.45 g, yield 74%).

m.p. 73.7° C.

PMR (CDCl$_3$) δ ppm: 0.98 (t, 3H, —CH$_2$CH$_2$CH$_3$, J=6.0 Hz) 2.54 (s, 3H, —CH$_3$) 6.86 (s, 1H, pyrimidine-H$^5$) 7.65 (t, 1H, pyridine-H$^4$, J=7.2 Hz) 8.07 (d, 1H, pyridine-H$^3$, J=7.2 Hz).

EXAMPLE 4

To 6-(p-chloro-o-methylphenoxy)-2-picoline amidine hydrochloride (2 g) was added malonaldehyde bis(dimethylacetal) (3.3 g). The mixture was heated about 120° C. for an hour, and then concentrated under reduced pressure.

The residue obtained was subjected to silica-gel column chromatography (eluent; n-hexane: ethylacetate=1:1 in volume) to obtain 2-(6-(p-chloro-o-methylphenoxy)-2-pyridinyl)pyrimidine (1.2 g, yield 60%).

m.p. 105.3° C.

PMR (CDCl$_3$) δ ppm: 2.22 (s, 3H, —CH$_3$) 7.78 (t, 1H, pyridine-H$^4$, J=7.8 Hz) 8.23 (d, 1H, pyridine-H$^3$, J=7.8 Hz) 8.89 (d, 2H, pyrimidine H$^4$ and H$^6$, J=4.8 Hz).

EXAMPLE 5

To N,N-dimethylformamide (50 ml) were added 2,4-dimethylphenol (1.46 g) and potassium carbonate (0.83 g), and then the mixture was stirred for 30 minutes at room temperature. 2-(6-Bromo-2-pyridinyl)-4-methylpyrimidine (2 g) and cuprous chloride (0.1 g) were added thereto, and the mixture was further heated under refluxing for 2 hours.

After the reaction mixture was cooled to room temperature, water (50 ml) and ethylacetate (100 ml) were added thereto, and then extracted. After the extract was dried over anhydrous magnesium sulfate, it was concentrated under reduced pressure. The residue was subjected to silica-gel column chromategraphy (eluent; n-hexane: ethyl acetate=2:1 in volume) to give 2-(6-(2,4-dimethylphenoxy)-2-pyridinyl)-4-methylpyrimidine (1.65 g, yield 71%).

$n_D^{25}$ 1.6048.

PMR (CDCl$_3$) δ ppm: 2.22 (s, 3H, —CH$_3$) 2.34 (s, 3H, —CH$_3$) 2.65 (s, 3H, —CH$_3$) 7.75 (t, 1H, pyridine-H$^4$, J=7.2 Hz) 8.21 (d, 1H, pyridine-H$^3$, J=7.2 Hz) 8.76 (d, 1H, pyridmidine-H$^6$, J=6.0 Hz)

Some of compounds of this invention which are prepared according to the similar procedures to the above are listed in Table 1.

TABLE 1

Pyridinylpyrimidine derivatives

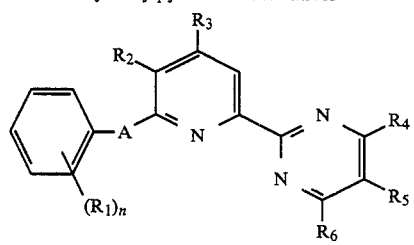

| Compound No. | (R$_1$)$_n$ | A | R$_2$ | R$_3$ | R$_4$ | R$_5$ | R$_6$ | Physical constant |
|---|---|---|---|---|---|---|---|---|
| 1 | phenyl | O | H | H | CH$_3$ | H | H | $n_D^{23}$ 1.6052 |
| 2 | 2-Cl-phenyl | O | H | H | CH$_3$ | H | H | m.p. 128.7° C. |
| 3 | 2-Cl-phenyl | O | H | H | n-C$_3$H$_7$ | H | CH$_3$ | m.p. 73.7° C. |
| 4 | 2-Cl-phenyl | O | CH$_3$ | H | CH$_3$ | H | H | m.p. 124.2° C. |

TABLE 1-continued
Pyridinylpyrimidine derivatives
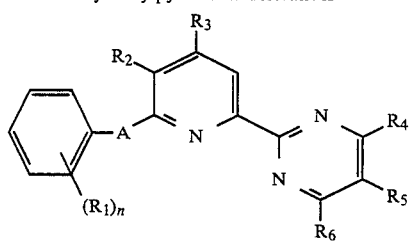
| Compound No. | (R₁)ₙ | A | R₂ | R₃ | R₄ | R₅ | R₆ | Physical constant |
|---|---|---|---|---|---|---|---|---|
| 5 | 2-Cl-phenyl | O | H | CH₃ | CH₃ | H | H | m.p. 142.8° C. |
| 6 | 3-Cl-phenyl | O | H | H | CH₃ | H | H | m.p. 108.3° C. |
| 7 | 4-Cl-phenyl | O | H | H | CH₃ | H | H | m.p. 107.2° C. |
| 8 | 2,4-diCl-phenyl | O | H | H | CH₃ | H | H | m.p. 151.7° C. |
| 9 | 2-F-phenyl | O | H | H | CH₃ | H | H | m.p. 152.0° C. |
| 10 | 4-F-phenyl | O | H | H | CH₃ | H | H | m.p. 86.1° C. |
| 11 | 4-Br-phenyl | O | H | H | CH₃ | H | H | m.p. 110.4° C. |
| 12 | 2-I-phenyl | O | H | H | CH₃ | H | H | $n_D^{27}$ 1.6242 |

TABLE 1-continued

Pyridinylpyrimidine derivatives

| Compound No. | (R₁)ₙ | A | R₂ | R₃ | R₄ | R₅ | R₆ | Physical constant |
|---|---|---|---|---|---|---|---|---|
| 13 | 4-Br, 3-Cl-phenyl | O | H | H | CH₃ | H | H | m.p. 151.1° C. |
| 14 | 4-Cl, 2-CH₃-phenyl | O | H | H | CH₃ | H | H | m.p. 111.7° C. |
| 15 | 4-Cl, 2-CH₃-phenyl | O | H | H | H | H | H | m.p. 105.3° C. |
| 16 | 2-Br, 3,5-(CH₃)₂-phenyl | O | H | H | CH₃ | H | H | m.p. 110.6° C. |
| 17 | 2-CH₃-phenyl | O | H | H | CH₃ | H | H | m.p. 121.0° C. |
| 18 | 3-CH₃-phenyl | O | H | H | CH₃ | H | H | $n_D^{26.5}$ 1.5960 |
| 19 | 4-CH₃-phenyl | O | H | H | CH₃ | H | H | $n_D^{21.5}$ 1.6065 |
| 20 | 4-CH₃-phenyl | S | H | H | CH₃ | H | H | m.p. 99.2° C. |

TABLE 1-continued
Pyridinylpyrimidine derivatives
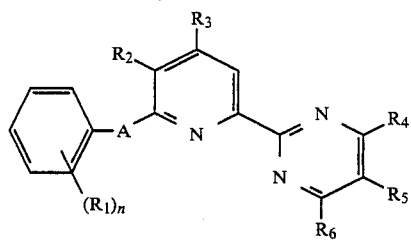
| Compound No. | (R₁)ₙ | A | R₂ | R₃ | R₄ | R₅ | R₆ | Physical constant |
|---|---|---|---|---|---|---|---|---|
| 21 | 2-CH₃-phenyl | O | CH₃ | H | CH₃ | H | H | m.p. 64.8° C. |
| 22 | 2,4-(CH₃)₂-phenyl | O | H | H | CH₃ | H | H | $n_D^{25}$ 1.6048 |
| 23 | 2,4-(CH₃)₂-phenyl | O | H | H | H | H | H | $n_D^{26}$ 1.6066 |
| 24 | 2,6-(CH₃)₂-phenyl | O | H | H | CH₃ | H | H | $n_D^{25}$ 1.5902 |
| 25 | 2,4,6-(CH₃)₃-phenyl | O | H | H | CH₃ | H | H | $n_D^{25}$ 1.5831 |
| 26 | 2-n-C₃H₇-phenyl | O | H | H | CH₃ | H | H | $n_D^{23}$ 1.5888 |
| 27 | 4-iso-C₃H₇-phenyl | O | H | H | CH₃ | H | H | $n_D^{21.5}$ 1.5771 |

TABLE 1-continued
Pyridinylpyrimidine derivatives
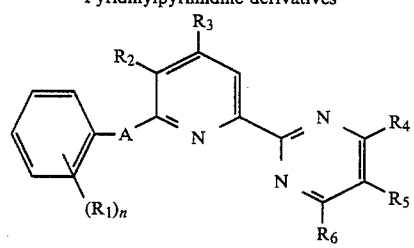
| Compound No. | (R₁)ₙ | A | R₂ | R₃ | R₄ | R₅ | R₆ | Physical constant |
|---|---|---|---|---|---|---|---|---|
| 28 | 2-COOCH₃-C₆H₄- | O | H | H | CH₃ | H | H | $n_D^{26.5}$ 1.5919 |
| 29 | 4-CN-C₆H₄- | O | H | H | CH₃ | H | H | m.p. 150.0° C. |
| 30 | 4-CH₃S-C₆H₄- | O | H | H | CH₃ | H | H | $n_D^{23}$ 1.6234 |
| 31 | 2-OCH₃-C₆H₄- | O | H | H | CH₃ | H | H | m.p. 72.0° C. |
| 32 | 2-OC₂H₅-C₆H₄- | O | H | H | CH₃ | H | H | m.p. 88.3° C. |
| 33 | 4-C₂H₅O-C₆H₄- | O | H | H | CH₃ | H | H | m.p. 61.2° C. |
| 34 | 4-C₂H₅O-C₆H₄- | O | H | H | CH₃ | CH₃ | H | m.p. 102.1° C. |
| 35 | 4-C₂H₅O-C₆H₄- | O | H | H | CH₃ | H | OCH₃ | m.p. 135.8° C. |
| 26 | 4-C₂H₅O-C₆H₄- | O | H | H | CH₃ | H | OCH₂CH=CH₂ | m.p. 59.8° C. |

TABLE 1-continued
Pyridinylpyrimidine derivatives
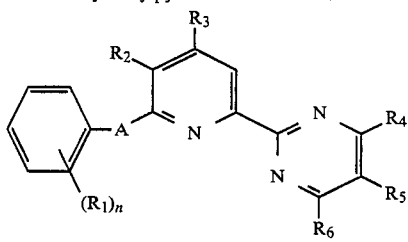
| Compound No. | (R₁)ₙ | A | R₂ | R₃ | R₄ | R₅ | R₆ | Physical constant |
|---|---|---|---|---|---|---|---|---|
| 37 | C₂H₅O—⟨phenyl⟩— | O | H | H | CH₃ | H | OCH₂C≡CH | m.p. 85.8° C. |
| 38 | ⟨2-CF₃-phenyl⟩— | O | H | H | CH₃ | H | H | m.p. 72.4° C. |
| 39 | CF₃—⟨phenyl⟩— | O | H | H | CH₃ | H | H | m.p. 88.8° C. |
| 40 | ⟨biphenyl⟩— | O | H | H | CH₃ | H | H | $n_D^{22}$ 1.6415 |
| 41 | ⟨2-CH₃-4,5-diCl-phenyl⟩— | O | H | H | CH₃ | H | H | m.p. 129.3° C. |
| 42 | ⟨phenyl⟩— | O | CH₃ | H | CH₃ | H | H | m.p. 99.7° C. |
| 43 | ⟨phenyl⟩— | O | H | H | CH₃ | H | OCH₃ | m.p. 69.4° C. |
| 44 | ⟨3-CH₃-phenyl⟩— | O | CH₃ | H | CH₃ | H | H | m.p. 64.8° C. |

TABLE 1-continued

Pyridinylpyrimidine derivatives

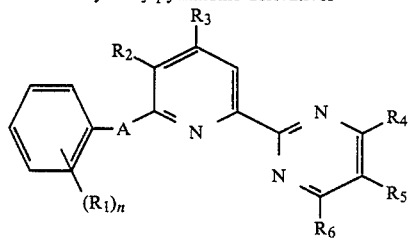

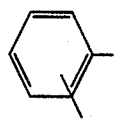

| Compound No. | (R₁)ₙ | A | R₂ | R₃ | R₄ | R₅ | R₆ | Physical constant |
|---|---|---|---|---|---|---|---|---|
| 45 | CH₃, Cl- (phenyl) | O | CH₃ | H | CH₃ | H | H | m.p. 130.1° C. |

The following reference examples show the preparation of various starting compounds.

REFERENCE EXAMPLE 1

Preparation of picoline amidine derivative (III) (HCl-salt)

6-o-Chlorophenoxy-2-cyanopyridine (10 g) was dissolved in a solution of sodium methoxide in methanol prepared from methanol (150 ml) and metallic sodium (0.50 g). After the solution was left to stand overnight, acetic acid (1.3 g) was added thereto, followed by concentration under reduced pressure. The resulting residue was dissolved in ether (200 ml) and insoluble materials were filtered out. The filtrate was concentrated under reduced pressure to obtain methyl 2-picoline imidate derivative.

To the imidate derivative obtained above was added a solution of ammonium chloride (2.2 g) in water (10 ml) and ethanol (50 ml) and the mixture was heated under refluxing for one hour. After being left to stand to cool, the reaction mixture was concentrated under reduced pressure. The crystalline residue obtained was washed with acetone to obtain 6-o-chlorophenoxy-2-picoline amidine hydrochloride (10.8 g).
m.p. 158.0° C.

Some of picoline amidine derivatives or salts thereof having the formula (III) which are able to prepare according to the similar procedure to the above are listed in Table 2.

TABLE 2

Picoline amidine derivative or their salts

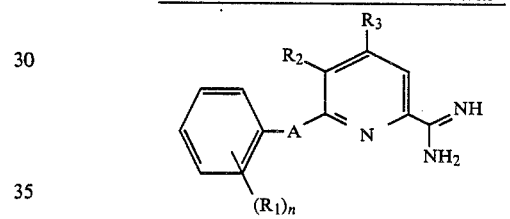

| (R₁)ₙ | A | R₂ | R₃ | Physical constant |
|---|---|---|---|---|
| o-Cl-phenyl | O | H | H | m.p. 158.0° C. (HCl salt) |
| o-Cl-phenyl | O | CH₃ | H | m.p. 216.0° C. (HCl salt) |
| o-Cl-phenyl | O | H | CH₃ | m.p. 120.0° C. (HCl salt) |
| 2,4-di-Cl-phenyl | O | H | H | m.p. 134.4° C. (HCl salt) |

TABLE 2-continued

Picoline amidine derivative or their salts

[Structure: pyridine ring with substituents R2, R3, and phenyl group bearing (R1)n linked via A, with amidine group -C(=NH)NH2]

| (R1)n | A | R2 | R3 | Physical constant |
|---|---|---|---|---|
| 2,6-dichlorophenyl | O | H | H | m.p. 237.7° C. (HCl salt) |
| 2,4-dichloro-6-methylphenyl | O | H | H | m.p. 240.5° C. (HCl salt) |
| 4-chloro-2-methylphenyl | O | H | H | m.p. 125.0° C. (HCl salt) |
| 2-methylphenyl | O | CH3 | H | m.p. 187.0° C. (HCl salt) |
| 4-methylphenyl | O | H | H | m.p. 166.0° C. (HCl salt) |
| 4-isopropylphenyl | O | H | H | m.p. 147.5° C. (HCl salt) |
| 2-methoxyphenyl | O | H | H | m.p. 159.7° C. (HCl salt) |

REFERENCE EXAMPLE 2

Preparation of hydroxypyrimidine derivative (XVIII)

6-o-Chlorophenoxy-2-picoline amidine hydrochloride (5 g) was dissolved in a solution of sodium ethoxide in ethanol prepared from ethanol (100 ml) and metallic sodium (0.53 g).

Ethyl butyrylacetate (3.34 g) was added to the solution obtained above, then the mixture was heated under refluxing for one hour. After the reaction mixture was cooled to room temperature, it was neutralized with acetic acid and then concentrated under reduced pressure. The residue obtained was washed with water and n-hexane to obtain 2-(6-o-chlorophenoxy-2-pyridinyl)-4-hydroxy-6-n-propylpyrimidine (5.0 g, yield 83%).

m.p. 95.1° C.

PMR (CDCl3) δ ppm: 0.97 (t, 3H, —CH2CH2CH3, J=6.6 Hz) 6.16 (s, 1H, pyrimidine-H$^5$).

REFERENCE EXAMPLE 3

Preparation of halopyrimidine derivative (VI)

To solution of 2-(6-o-chlorophenoxy-2-pyridinyl)-4-hydroxy-6-n-propylprimidine (5 g) in toluene (100 ml), was added phosphoryl chloride (5 g). The mixture was heated under refluxing for one hour and left to stand to room temperature. Aqueous sodium carbonate solution was added thereto until the reaction solution became about pH 8 to be separated into two layers. Toluene layer was washed with water and dried over anhydrous magnesium sulfate. The toluene layer was concentrated under reduced pressure to obtain 4-chlono-2-(6-o-chlorophenoxy-2-pyridinyl)-6-n-propylpyrimidine (4.6 g, yield 87%).

m.p. 96.5° C.

PMR (CDCl3) δ ppm: 0.97 (t, 3H, —CH2CH2CH3, J=6.6 Hz) 7.20 (t, 1H, pyridine-H$^4$, J=7.2 Hz) 8.11 (d, 1H, pyridine-H$^3$, J=7.2 Hz).

REFERENCE EXAMPLE 4

Preparation of picoline amidine derivative (XXII) (HCl-salt)

6-Bromo-2-cyano-pyridine (20 g) was dissolved in a solution of sodium methoxide in methanol prepared from methanol (300 ml) and metallic sodium (1.26 g). After the solution was left to stand for 15 minutes, acetic acid (3.3 g) was added thereto, followed by concentration under reduced pressure. The resulting residue was dissolved in ether (300 ml) and insoluble materials were filtered out. The filtrate was concentrated under reduced pressure to obtain methyl 2-picoline imidate derivative.

To the imidate derivative obtained above was added a solution of ammonium chloride (5.54 g) in water (30 ml) and ethanol (120 ml) and the mixture was heated under refluxing for one hour. After being left to stand to cool, the reaction mixture was concentrated under reduced pressure. The crystalline residue obtained was washed with acetone to obtain 6-bromo-2-picoline amidine hydrochloride (21 g).

m.p. 212.3° C.

Some of picoline amidine derivatives or salts thereof having the formula (XXII) which are able to prepare according to the similar procedure to the above are listed in Table 3.

TABLE 3

Picoline amidine derivative or their salts

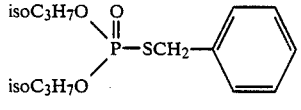

| Z | R₂ | R₃ | Physical constant |
|---|---|---|---|
| Br | H | H | m.p. 212.3° C. (HCl salt) |
| Br | CH₃ | H | m.p. 225.0° C. (HCl salt) |

REFERENCE EXAMPLE 5

Preparation of pyridinylpyrimidine derivative (XII)

To a mixture of 6-bromo-2-picoline amidine hydrochloride (10 g) and methanol (200 ml) were added 28% sodium methoxide solution in methanol (10.6 g) and 1,1-dimethoxy-3-butanone (6.1 g). The mixture was heated under refluxing for an hour, and then concentrated under reduced pressure. Water (100 ml) and ethylacetate (200 ml) were added thereto, and then extracted. After the extract was dried over anhydrous magnesium sulfate, it was concentrated under reduced pressure. The residue was washed with n-hexane to obtain 2-(6-bromo-2-pyridinyl)-4-methylpyrimidine (8.9 g, yield 84%).

m.p. 126.8° C.

PMR (CDCl₃) δ ppm: 2.66 (s, 3H, —CH₃) 7.22 (d, 1H, pyrimidine-$H^5$, J=5.4 Hz) 8.82 (d, 1H, pyrimidine-$H^6$, J=5.4 Hz).

Some of pyridinylpyrimidine derivatives having the formula (XII) which are able to prepare according to the similar procedure to the above are listed in Table 4.

TABLE 4

Pyridinylpyrimidine derivative

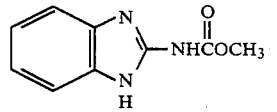

| Z | R₂ | R₃ | R₄ | R₅ | R₆' | Physical constant |
|---|---|---|---|---|---|---|
| Br | H | H | CH₃ | H | H | m.p. 126.8° C. |
| Br | CH₃ | H | CH₃ | H | H | m.p. 85.0° C. |

FORMULATION EXAMPLES

The present compounds used are identified by numbers shown in Table 1. Quantities are expressed by parts by weight.

FORMULATION EXAMPLE 1

A wettable powder each is prepared by mixing and pulverizing 50 parts of each of the present compounds (1)–(45), 3 parts of calcium ligninsulfonate, 2 parts of sodium lauryl sulfate and 45 parts of synthetic hydrated silica.

FORMULATION EXAMPLE 2

A suspension each is prepared by mixing 25 parts of each of the present compounds (1)–(45), 3 parts of polyoxyethylene sorbitanmonooleate, 3 parts of CMC and 69 parts of water, followed by wet grinding to give a particle size smaller than 5 microns.

FORMULATION EXAMPLE 3

A dust each is prepared by mixing and pulverizing 2 parts of each of the present compounds (1)–(45), 88 parts of kaolin clay and 10 parts of talc.

FORMULATION EXAMPLE 4

An emulsifiable concentrate each is prepared by thoroughly mixing 20 parts of each of the present compounds (1)–(45), 14 parts of polyoxyethylene styrylphenyl ether, 6 parts of calcium dodecylbenzenesulfonate and 60 parts of xylene.

FORMULATION EXAMPLE 5

A granule each is prepared by mixing and pulverizing 2 parts of each of the present compounds (1)–(45), 1 part of synthetic hydrated silica, 2 parts of calcium ligninsulfonate, 30 parts of bentonite and 65 parts of kaolin clay, followed by kneading with water, granulation and drying.

The following test examples demonstrate the effectiveness of the present compound used as an active ingredient of fungicides. The present compounds used in the test examples are identified by the compound numbers shown in Table 1, and the compounds used for control are identified by the compound symbols shown in Table 5.

TABLE 5

| Compound symbol | Compound | Remarks |
|---|---|---|
| A | 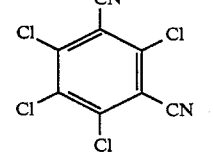 | Commercial fungicide "IBP" |
| B | benzimidazole-NHCOCH₃ structure | Commercial fungicide "MBC" |
| C | tetrachloroisophthalonitrile structure | Commercial fungicide "TPN" |

The controlling effect was evaluated by visually observing the degree of fungus colony and infected area of the leaved and stems of the test plants. The results of evaluation were expressed in terms of six ratings as follows:

"5" Not observed at all.
"4" Observed on about 10% of the leaves and stems.
"3" Observed on about 30% of the leaves and stems.
"2" Observed on about 50% of the leaves and stems.
"1" Observed on about 70% of the leaves and stems.
"0" Same as control.

TEST EXAMPLE 1

Test for preventive controlling effect on blast (*Pyricularia oryzae*) of rice

Rice seeds (var.: Kinki No. 33) were sown in the sandy loam filled in a plastic pot. After raising for 20 days in a greenhouse, the seedings were subjected to foliage application with a spray liquid of the emulsion prepared according to Formulation example 4 which was diluted with water to the given concentrations. After application, the seedlings were air-dried and then inoculated with spores of *Pyricularia oryzae* by spraying a suspension of spores. The inoculated seedlings were grown in a dark damp place at 28° C. for 4 days, and the controlling effect was examined. The results are shown in Table 6.

TABLE 6

| Compound No. | Concentration of active ingredient (ppm) | Control effect |
| --- | --- | --- |
| Present compound | | |
| (1) | 100 | 5 |
| (2) | 100 | 5 |
| (3) | 100 | 5 |
| (4) | 100 | 5 |
| (5) | 100 | 5 |
| (6) | 100 | 5 |
| (7) | 100 | 5 |
| (8) | 100 | 5 |
| (9) | 100 | 5 |
| (10) | 100 | 5 |
| (11) | 100 | 5 |
| (12) | 100 | 5 |
| (13) | 100 | 5 |
| (14) | 100 | 5 |
| (15) | 100 | 5 |
| (16) | 100 | 5 |
| (17) | 100 | 5 |
| (18) | 100 | 5 |
| (19) | 100 | 5 |
| (20) | 100 | 5 |
| (21) | 100 | 5 |
| (22) | 100 | 5 |
| (23) | 100 | 5 |
| (24) | 100 | 5 |
| (25) | 100 | 5 |
| (26) | 100 | 5 |
| (27) | 100 | 5 |
| (28) | 100 | 5 |
| (29) | 100 | 5 |
| (30) | 100 | 5 |
| (31) | 100 | 5 |
| (32) | 100 | 5 |
| (33) | 100 | 5 |
| (34) | 100 | 5 |
| (35) | 100 | 5 |
| (36) | 100 | 5 |
| (37) | 100 | 5 |
| (38) | 100 | 5 |
| (39) | 100 | 5 |
| (40) | 100 | 5 |
| (41) | 100 | 5 |
| (42) | 100 | 5 |
| (43) | 100 | 5 |
| (44) | 100 | 5 |
| (45) | 100 | 5 |
| Reference compound A | 200 | 4 |

TEST EXAMPLE 2

Test for curative controlling effect on blast (*Pyricularia oryzae*) of rice

Rice seeds (var.: Kinki No. 33) were sown in the sandy loam filled in a plastic pot. After raising for 20 days in a greenhouse, the seedlings were inoculated with spores of *Pyricularia oryzae* by spraying a suspension of spores. The inoculated seedlings were grown in a dark damp place at 28° C. for 16 hours. The seedlings were subjected to foliage application with a spray liquid of the emulsion prepared according to Formulation example 4 which was diluted with water to the given concentrations. After application, the seedlings were grown in a dark damp place at 28° C. for 3 days, and the controlling effect was examined. The results are shown in Table 7.

TABLE 7

| Compound No. | Concentration of active ingredient (ppm) | Control effect |
| --- | --- | --- |
| Present compound | | |
| (1) | 100 | 5 |
| (2) | 100 | 5 |
| (3) | 100 | 5 |
| (4) | 100 | 5 |
| (5) | 100 | 5 |
| (6) | 100 | 5 |
| (7) | 100 | 5 |
| (8) | 100 | 5 |
| (9) | 100 | 5 |
| (10) | 100 | 5 |
| (11) | 100 | 5 |
| (12) | 100 | 5 |
| (13) | 100 | 5 |
| (14) | 100 | 5 |
| (15) | 100 | 5 |
| (16) | 100 | 5 |
| (17) | 100 | 5 |
| (18) | 100 | 5 |
| (19) | 100 | 5 |
| (20) | 100 | 5 |
| (21) | 100 | 5 |
| (22) | 100 | 5 |
| (23) | 100 | 5 |
| (24) | 100 | 5 |
| (26) | 100 | 5 |
| (27) | 100 | 5 |
| (28) | 100 | 5 |
| (29) | 100 | 5 |
| (30) | 100 | 5 |
| (31) | 100 | 5 |
| (32) | 100 | 5 |
| (33) | 100 | 5 |
| (34) | 100 | 5 |
| (35) | 100 | 5 |
| (36) | 100 | 5 |
| (37) | 100 | 5 |
| (38) | 100 | 5 |
| (39) | 100 | 5 |
| (40) | 100 | 5 |
| (41) | 100 | 5 |
| (42) | 100 | 5 |
| (43) | 100 | 5 |
| (44) | 100 | 5 |
| (45) | 100 | 5 |
| Reference compound A | 500 | 4 |

TEST EXAMPLE 3

Test for curative controlling effect on powdery mildew (*Erysiphe graminis* f. sp. *tritici*) of wheat Wheat seeds (var.: Nohrin No. 78) were sown in the sandy loam filled in a plastic pot. After raising for 10 days in a greenhouse, the seedlings were inoculated with spores of *Erysiphe graminis* f. sp. *tritici*. The inoculated seedlings were grown at 23° C. for 3 days. The seedlings were subjected to foliage application with a spray liquid of the wettable powder prepared according to Formulation example 1 which was diluted with water to the given concentrations. After application, the seedlings were grown in a greenhouse at 23° C. for 7 days, and the controlling effect was examined. The results are shown in Table 8.

TABLE 8

| Compound No. | Concentration of active ingredient (ppm) | Control effect |
| --- | --- | --- |
| Present Compound | | |
| (1) | 400 | 5 |
| (9) | 400 | 5 |
| (10) | 400 | 5 |
| (11) | 400 | 5 |
| (17) | 400 | 5 |
| (18) | 400 | 5 |
| (24) | 400 | 5 |
| (26) | 400 | 5 |
| (42) | 400 | 5 |
| (43) | 400 | 5 |
| (44) | 400 | 5 |

TEST EXAMPLE 4

Test for preventive controlling effect on glume blotch (*Septoria nodorum*) of wheat A plastic pot was filled with sandy loam, and seeds of wheat (var.: Nohrin No. 73) were sowed therein and grown in a greenhouse for 8 days. The test compound formulated in a wettable powder according to Formulation example 1 and diluted with water to a designed concentration was thoroughly sprayed over the plants. And after air-drying a spore suspension of *Septoria nodorum* was inoculated to the seedlings of the test plants by spraying. The plants were kept at 15° C. under dark and humid conditions for 1 day and grown under illumination for 10 days and subject to observation for the preventive controlling effect. The results are shown in Table 9.

TABLE 9

| Compound No. | Concentration of active ingredient (ppm) | Control effect |
| --- | --- | --- |
| Present Compound | | |
| (1) | 400 | 5 |
| (2) | 400 | 5 |
| (3) | 400 | 5 |
| (4) | 400 | 5 |
| (5) | 400 | 5 |
| (6) | 400 | 5 |
| (7) | 400 | 5 |
| (8) | 400 | 5 |
| (9) | 400 | 5 |
| (10) | 400 | 5 |
| (11) | 400 | 5 |
| (12) | 400 | 5 |
| (13) | 400 | 5 |
| (14) | 400 | 5 |
| (15) | 400 | 5 |
| (16) | 400 | 5 |
| (17) | 400 | 5 |
| (18) | 400 | 5 |
| (19) | 400 | 5 |
| (20) | 400 | 5 |
| (21) | 400 | 5 |
| (22) | 400 | 5 |
| (23) | 400 | 5 |
| (24) | 400 | 5 |
| (25) | 400 | 5 |
| (26) | 400 | 5 |
| (27) | 400 | 5 |
| (28) | 400 | 5 |
| (29) | 400 | 5 |
| (30) | 400 | 5 |
| (31) | 400 | 5 |
| (32) | 400 | 5 |

TABLE 9-continued

| Compound No. | Concentration of active ingredient (ppm) | Control effect |
| --- | --- | --- |
| (33) | 400 | 5 |
| (34) | 400 | 5 |
| (35) | 400 | 5 |
| (36) | 400 | 5 |
| (37) | 400 | 5 |
| (38) | 400 | 5 |
| (39) | 400 | 5 |
| (40) | 400 | 5 |
| (41) | 400 | 5 |
| (42) | 400 | 5 |
| (43) | 400 | 5 |
| (44) | 400 | 5 |
| (45) | 400 | 5 |

TEST EXAMPLE 5

Test for preventive controlling effect on net blotch (*Pyrenophora teres*) of barley A plastic pot was filled with sandy loam, and seeds of barley (var.: Sekijinriki) were sowed therein and grown in a greenhouse for 7 days. The test compound formulated in an emulsion according to Formulation example 4 and diluted with water to a designed concentration was thoroughly sprayed over the seedlings of the test plants and, after air-drying, a spore suspension of *Pyrenophora teres* was inoculated thereto by spraying. The plants were kept at 15° C. under a humid condition for 1 day, taken out from the humid condition, then grown at 15° C. for 17 days and subjected to observation for the preventive controlling effect. The results are shown in Table 10.

TABLE 10

| Compound No. | Concentration of active ingredient (ppm) | Control effect |
| --- | --- | --- |
| Present Compound | | |
| (1) | 400 | 5 |
| (2) | 400 | 5 |
| (3) | 400 | 5 |
| (4) | 400 | 5 |
| (5) | 400 | 5 |
| (6) | 400 | 5 |
| (7) | 400 | 5 |
| (8) | 400 | 5 |
| (9) | 400 | 5 |
| (10) | 400 | 5 |
| (11) | 400 | 5 |
| (12) | 400 | 5 |
| (13) | 400 | 5 |
| (14) | 400 | 5 |
| (15) | 400 | 5 |
| (16) | 400 | 5 |
| (17) | 400 | 5 |
| (18) | 400 | 5 |
| (20) | 400 | 5 |
| (21) | 400 | 5 |
| (22) | 400 | 5 |
| (23) | 400 | 5 |
| (24) | 400 | 5 |
| (25) | 400 | 5 |
| (26) | 400 | 5 |
| (27) | 400 | 5 |
| (28) | 400 | 5 |
| (29) | 400 | 5 |
| (30) | 400 | 5 |
| (31) | 400 | 5 |
| (32) | 400 | 5 |
| (33) | 400 | 5 |
| (34) | 400 | 5 |
| (35) | 400 | 5 |
| (36) | 400 | 5 |
| (37) | 400 | 5 |

TABLE 10-continued

| Compound No. | Concentration of active ingredient (ppm) | Control effect |
|---|---|---|
| (38) | 400 | 5 |
| (39) | 400 | 5 |
| (40) | 400 | 5 |
| (41) | 400 | 5 |
| (42) | 400 | 5 |
| (43) | 400 | 5 |
| (44) | 400 | 5 |
| (45) | 400 | 5 |

TEST EXAMPLE 6

Test for preventive controlling effect on leaf blotch (*Rhynchosporium secalis*) of barley A plastic pot was filled with sandy loam, and seeds of barley (var.: Sekijinriki) were sowed therein and grown in a greenhouse for 10 days. The test compound formulated in an emulsion according to Formulation example 4 and diluted with water to a designed concentration was thoroughly sprayed over the seedlings of the test plants and, after air-drying, a spore suspension of *Rhynchosporium secalis* was inoculated thereto by spraying. The plants were kept at 15° C. under dark and humid conditions for 1 day and further under illumination for 14 days and subjected to observation for the preventive controlling effect. The results are shown in Table 11.

TABLE 11

| Compound No. | Concentration of active ingredient (ppm) | Control effect |
|---|---|---|
| Present compound | | |
| (6) | 400 | 5 |
| (10) | 400 | 5 |
| (14) | 400 | 5 |
| (16) | 400 | 5 |
| (19) | 400 | 5 |
| (25) | 400 | 5 |
| (27) | 400 | 5 |
| (32) | 400 | 5 |
| (33) | 400 | 5 |
| (43) | 400 | 5 |
| (44) | 400 | 5 |

TEST EXAMPLE 7

Test for curative controlling effect on eye spot (*Pseudocercosporella herpotrichoides*) of wheat A plastic pot was filled with sandy loam, and seeds of wheat (var.: Nohrin No. 73) were sowed therein and grown in a greenhouse for 10 days. A spore suspension of *Pseudocercosporella herpotrichoides* was inoculated thereto by spraying. The plants were kept at 15° C. under dark and humid conditions for 2 days. The test compound formulated in a wettable powder according to Formulation example 1 and diluted with water to a designed concentration was thoroughly sprayed to the seedlings and, after air-drying, further grown under illuminated and humid conditions for 14 days and subjected to observation for the curative controlling effect. The results are shown in Table 12.

TABLE 12

| Compound No. | Concentration of active ingredient (ppm) | Control effect |
|---|---|---|
| Present compound | | |
| (1) | 400 | 5 |

TABLE 12-continued

| Compound No. | Concentration of active ingredient (ppm) | Control effect |
|---|---|---|
| (2) | 400 | 5 |
| (3) | 400 | 5 |
| (4) | 400 | 5 |
| (5) | 400 | 5 |
| (6) | 400 | 5 |
| (7) | 400 | 5 |
| (8) | 400 | 5 |
| (9) | 400 | 5 |
| (10) | 400 | 5 |
| (11) | 400 | 5 |
| (12) | 400 | 5 |
| (13) | 400 | 5 |
| (14) | 400 | 5 |
| (15) | 400 | 5 |
| (16) | 400 | 5 |
| (17) | 400 | 5 |
| (18) | 400 | 5 |
| (19) | 400 | 5 |
| (20) | 400 | 5 |
| (21) | 400 | 5 |
| (22) | 400 | 5 |
| (23) | 400 | 5 |
| (24) | 400 | 5 |
| (25) | 400 | 5 |
| (26) | 400 | 5 |
| (27) | 400 | 5 |
| (28) | 400 | 5 |
| (29) | 400 | 5 |
| (30) | 400 | 5 |
| (31) | 400 | 5 |
| (32) | 400 | 5 |
| (33) | 400 | 5 |
| (34) | 400 | 5 |
| (35) | 400 | 5 |
| (36) | 400 | 5 |
| (37) | 400 | 5 |
| (38) | 400 | 5 |
| (39) | 400 | 5 |
| (40) | 400 | 5 |
| (41) | 400 | 5 |
| (42) | 400 | 5 |
| (43) | 400 | 5 |
| (44) | 400 | 5 |
| (45) | 400 | 5 |

TEST EXAMPLE 8

Test for preventive controlling effect on scab (*Venturia inaequalis*) of apple

Apple seeds were sown in the sandy loam filled in a plastic pot. After raising for 20 days in a greenhouse, the seedlings, with the fourth to fifth foliage leaves open, were subjected to foliage application with a spray liquid of the emulsion prepared according to Formulation example 4 which was diluted with water to the given concentrations. After application, the seedlings were air-dried and then inoculated with spores of *Venturia inaequalis* by spraying a suspension containing the spores. The inoculated seedlings were grown in a dark damp place at 15° C. for 4 days, and then grown under lightening for 15 days. The controlling effect was examined. The results are shown in Table 13.

TABLE 13

| Compound No. | Concentration of active ingredient (ppm) | Control effect |
|---|---|---|
| Present compound | | |
| (1) | 400 | 5 |
| (2) | 400 | 5 |
| (3) | 400 | 5 |
| (4) | 400 | 5 |
| (5) | 400 | 5 |

TABLE 13-continued

| Compound No. | Concentration of active ingredient (ppm) | Control effect |
|---|---|---|
| (6) | 400 | 5 |
| (7) | 400 | 5 |
| (9) | 400 | 5 |
| (10) | 400 | 5 |
| (11) | 400 | 5 |
| (14) | 400 | 5 |
| (19) | 400 | 5 |
| (21) | 400 | 5 |
| (26) | 400 | 5 |
| (32) | 400 | 5 |
| (33) | 400 | 5 |
| (38) | 400 | 5 |
| (39) | 400 | 5 |
| (42) | 400 | 5 |
| (43) | 400 | 5 |
| (44) | 400 | 5 |
| Reference compound C | 400 | 4 |

TEST EXAMPLE 9

Test for preventive controlling effect on gray mold (*Botrytis cinerea*) of cucumber Cucumber seeds (var.: Sagami hanjiro) were sown in the sandy loam filled in a plastic pot. After raising for 14 days in a greenhouse, the seedlings were subjected to foliage application with a spray liquid of the wettable powder prepared according to Formulation example 1 which was diluted with water to the given concentrations. After application, the seedlings were air-dried and then inoculated with mycelia of *Botrytis cinerea* which is resistant to benzimidazole-thiophanate fungicide. The inoculated seedlings were grown in a dark damp place at 15° C. for 3 days, and the controlling effect was examined. The results are shown in Table 14.

TABLE 14

| Compound No. | Concentration of active ingredient (ppm) | Control effect |
|---|---|---|
| Present compound | | |
| (1) | 400 | 4 |
| (2) | 400 | 5 |
| (6) | 400 | 5 |
| (7) | 400 | 5 |
| (9) | 400 | 5 |
| (10) | 400 | 5 |
| (11) | 400 | 5 |
| (14) | 400 | 5 |
| (15) | 400 | 5 |
| (19) | 400 | 5 |
| (20) | 400 | 4 |
| (27) | 400 | 4 |
| (32) | 400 | 4 |
| (33) | 400 | 5 |
| (34) | 400 | 5 |
| (35) | 400 | 5 |
| (38) | 400 | 5 |
| (39) | 400 | 5 |
| (43) | 400 | 4 |
| Reference compound B | 400 | 0 |

TEST EXAMPLE 10

Test for preventive controlling effect on sheath blight (*Rhizoctonia solani*) of rice Rice seeds (var.: Kinki No. 33) were sown in the sandy loam filled in a plastic pot. After raising, for 28 days in a greenhouse, the seedlings were subjected to foliage application with a spray liquid of the wettable powder prepared according to Formulation example 1 which was diluted with water to the given concentrations. After application, the seedlings were air-dried and then inoculated with mycelia of *Rhizoctonia solani* by spraying an agar suspension containing the fungi. The inoculated seedlings were grown in a dark damp place at 28° C. for 4 days, and the controlling effect was examined. The results are shown in Table 15.

TABLE 15

| Compound No. | Concentration of active ingredient (ppm) | Control effect |
|---|---|---|
| Present compound | | |
| (2) | 400 | 5 |
| (6) | 400 | 5 |
| (12) | 400 | 5 |
| (13) | 400 | 5 |
| (14) | 400 | 5 |
| (19) | 400 | 5 |
| (22) | 400 | 5 |
| (24) | 400 | 5 |
| (27) | 400 | 5 |
| (32) | 400 | 5 |

TEST EXAMPLE 11

Test for preventive controlling effect on anthracnose (*Colletotrichum lagenarium*) of cucumber Cucumber seeds (var.: Sagami hanjiro) were sown in the sandy loam filled in a plastic pot. After raising for 14 days in a greenhouse, the seedlings were subjected to foliage application with a spray liquid of the emulsion prepared according to Formulation example 4 which was diluted with water to the given concentrations. After application, the seedlings were air-dried and then inoculated with spores of *Colletotrichum lagenarium* by spraying a suspension containing the spores. The inoculated seedlings were left to stand in a dark damp place at 23° C. for one day and then were grown under lightening for 4 days. The controlling effect was examined. The results are shown in Table 16.

TABLE 16

| Compound No. | Concentration of active ingredient (ppm) | Control effect |
|---|---|---|
| Present compound | | |
| (16) | 400 | 5 |
| (19) | 400 | 5 |
| (27) | 400 | 5 |
| (33) | 400 | 5 |
| (43) | 400 | 5 |
| (44) | 400 | 5 |
| Reference compound C | 400 | 4 |

TEST EXAMPLE 12

Test for preventive controlling effect on leaf spot (*Septoria tritici*) of wheat A plastic pot was filled with sandy loam, and seeds of wheat (var.: Nohrin No. 73) were sowed therein and grown in a greenhouse for 8 days. The test compound formulated in an emulsion according to Formulation example 4 and diluted with water to a designed concentration was thoroughly sprayed over the plants. And after air-drying a spore suspension of *Septoria tritici* was inoculated to the seedlings of the test plants by spraying. The plants were kept at 15° C. under dark and humid conditions for 3 days and grown under illumination for 15 days and subject to observation for the preventive controlling effect. The results are shown in Table 17.

TABLE 17

| Compound No. | Concentration of active ingredient (ppm) | Control effect |
|---|---|---|
| Present compound | | |
| (1) | 400 | 5 |
| (2) | 400 | 5 |
| (3) | 400 | 5 |
| (4) | 400 | 5 |
| (5) | 400 | 5 |
| (6) | 400 | 5 |
| (7) | 400 | 5 |
| (8) | 400 | 5 |
| (9) | 400 | 5 |
| (10) | 400 | 5 |
| (11) | 400 | 5 |
| (12) | 400 | 5 |
| (13) | 400 | 5 |
| (14) | 400 | 5 |
| (15) | 400 | 5 |
| (16) | 400 | 5 |
| (17) | 400 | 5 |
| (18) | 400 | 5 |
| (19) | 400 | 5 |
| (20) | 400 | 5 |
| (21) | 400 | 5 |
| (22) | 400 | 5 |
| (23) | 400 | 5 |
| (24) | 400 | 5 |
| (25) | 400 | 5 |
| (26) | 400 | 5 |
| (27) | 400 | 5 |
| (28) | 400 | 5 |
| (29) | 400 | 5 |
| (30) | 400 | 5 |
| (31) | 400 | 5 |
| (32) | 400 | 5 |
| (33) | 400 | 5 |
| (34) | 400 | 5 |
| (35) | 400 | 5 |
| (36) | 400 | 5 |
| (37) | 400 | 5 |
| (38) | 400 | 5 |
| (39) | 400 | 5 |
| (40) | 400 | 5 |
| (41) | 400 | 5 |
| (42) | 400 | 5 |
| (43) | 400 | 5 |
| (44) | 400 | 5 |
| (45) | 400 | 5 |

We claim:

1. A pyridinylpyrimidine derivative of the formula:

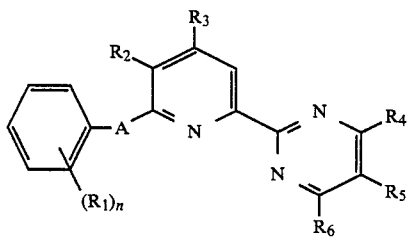

or a salt thereof, wherein
$R_1$ may be the same or different and is a $C_1$–$C_4$ alkyl group, a $C_1$–$C_3$ alkoxy group, a $C_1$–$C_3$ alkyl thio group, a cyano group, a carboalkoxy group whose alkoxy is a $C_1$–$C_3$ alkoxy group, a $C_1$–$C_3$ halo alkyl group, a phenyl group, or a halogen atom;
n is 0, 1, 2, 3, 4, or 5;
A is oxygen atom or sulfur atom;
$R_2$ and $R_3$, which may be the same or different, each represents a hydrogen atom, a methyl group, or an ethyl group;
$R_4$, and $R_5$, which may be the same or different, each represents a hydrogen atom or a $C_1$–$C_3$ alkyl group; and
$R_6$ is a hydrogen atom, a $C_1$–$C_4$ alkyl group, a $C_1$–$C_4$ alkoxy group, a $C_3$–$C_4$ alkenyloxy group, or a $C_3$–$C_4$ alkynyloxy group.

2. A pyridinylpyrimidine derivative according to claim 1, wherein $R_1$ may be the same or different and is a lower such as $C_1$–$C_3$ alkyl group, a methoxy group, an ethoxy group, a methylthio group, a lower such as $C_1$–$C_2$ haloalkyl group, or halogen atom; n is 0, 1, 2 or 3; A is oxygen atom; $R_2$ and $R_3$ which may be the same or different, each represents hydrogen atom or a methyl group; $R_4$ is a lower such as $C_1$–$C_3$ alkyl group; $R_5$ is hydrogen atom or a methyl group; $R_6$ is hydrogen atom, a methyl group, or a methoxy group.

3. A pyridinylpyrimidine derivative according to claim 1, wherein
$R_1$ may be the same or different and is a methyl group, a methoxy group, an ethoxy group, a trifluoromethyl group, fluorine, chlorine, or bromine;
n is 0, 1, or 2;
A is an oxygen;
$R_2$ and $R_3$, which may be the same or different, each represents a hydrogen atom, or a methyl group;
$R_4$ is a methyl group; and
$R_5$ and $R_6$ are hydrogen atoms.

4. A pyridinylpyrimidine derivative according to claim 1 wherein the derivative is selected from the group consisting of 2-(6-o-chlorophenoxy-2-pyridinyl)-4-methylpyrimidine, 4-methyl-2-(6-o-tolyloxy-2-pyridinyl)pyrimidine, 2-(6-p-ethoxyphenoxy-2-pyridinyl)-4-methylpyrimidine, 4-methyl-2-(5-methyl-6-o-tolyloxy-2-pyridinyl)pyrimidine, 2-(6-o-chlorophenoxy-5-methyl-2-pyridinyl)-4-methylpyrimidine.

5. A fungicidal composition which comprises as an active ingredient a fungicidally effective amount of a pyridinylpyrimidine derivative of the formula:

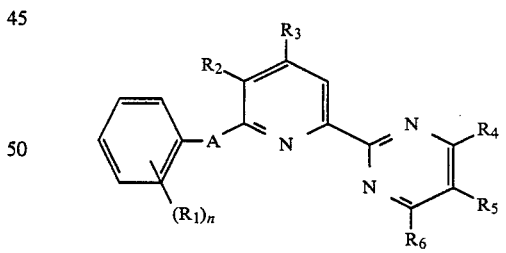

wherein $R_1$ may be the same or different and is an alkyl group, an alkoxy group, an alkyl thio group, a cyano group, a carboalkoxy group, halo alkyl group, a phenyl group, or halogen atom; n is 0, 1, 2, 3, 4, or 5; A is oxygen atom or sulfur atom; $R_2$, $R_3$, $R_4$ and $R_5$, which may be the same or different, each represents hydrogen atom or an alkyl group; $R_6$ is hydrogen atom, an alkyl group, an alkoxy group, an alkenyloxy group or an alkynyloxy group, or its salt, with an inert carrier.

6. A method for controlling plant pathogenic fungi which comprises applying a fungicidally effective amount of the pyridinylpyrimidine derivative of the formula:

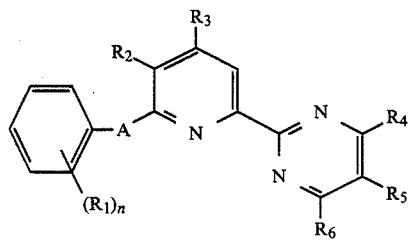
wherein $R_1$, $R_2$, $R_3$, $R_4$, $R_5$, $R_6$, A and n are as defined in claim 1, to plant phathogenic fungi.
* * * * *
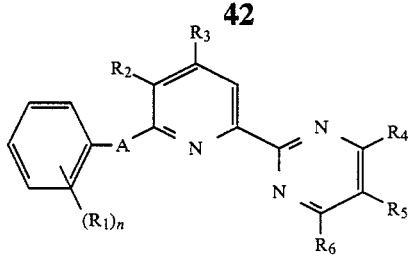
wherein $R_1$, $R_2$, $R_3$, $R_4$, $R_5$, $R_6$, A and n are as defined in claim 1, to plant phathogenic fungi.
* * * * *